United States Patent [19]

Hermeling

[11] Patent Number: 5,208,384
[45] Date of Patent: May 4, 1993

[54] 2-METHYLBENZALDEHYDE DIALKYL ACETALS

[75] Inventor: Dieter Hermeling, Frankenthal, Fed. Rep. of Germany

[73] Assignee: BASF Aktiengesellschaft, Ludwigshafen, Fed. Rep. of Germany

[21] Appl. No.: 841,982

[22] Filed: Feb. 26, 1992

[30] Foreign Application Priority Data

Mar. 2, 1991 [DE] Fed. Rep. of Germany ....... 4106661

[51] Int. Cl.$^5$ .............................................. C07C 45/00
[52] U.S. Cl. ................................... 568/426; 568/425; 568/591; 568/592
[58] Field of Search ............... 568/596, 425, 426, 591, 568/592

[56] References Cited

U.S. PATENT DOCUMENTS

| | | | |
|---|---|---|---|
| 3,928,421 | 12/1975 | Kyogoku et al. | 568/592 |
| 4,120,761 | 10/1978 | White | 568/592 |
| 4,284,825 | 8/1981 | Degner | 568/592 |
| 4,318,783 | 3/1982 | Buhmann et al. | 568/592 |
| 4,814,510 | 3/1989 | Degner et al. | 568/592 |
| 4,820,389 | 4/1989 | Degner et al. | 568/592 |

FOREIGN PATENT DOCUMENTS 12240 6/1980 European Pat. Off. ............ 568/592

Primary Examiner—Werren B. Lone
Attorney, Agent, or Firm—John H. Shurtleff

[57] ABSTRACT

2-Methylbenzaldehyde dialkyl acetals of the general formula I

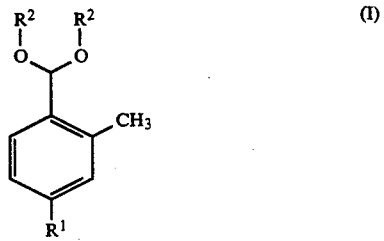

where $R^1$ is $C_3$-$C_{20}$-alkyl or $C_1$-$C_{12}$-alkoxy and $R^2$ is $C_1$-$C_8$-alkyl, with the proviso that $R^1$ is not methoxy when $R^2$ is methyl, are prepared and are used for the preparation of 2-methylbenzaldehydes.

11 Claims, No Drawings

2-METHYLBENZALDEHYDE DIALKYL ACETALS

The present invention relates to novel 2-methylbenzaldehyde dialkyl acetals, their preparation and their use as stable forms of substituted 2-methylbenzaldehydes.

EP-A-12 240 and DE-A-37 13 732 disclose benzaldehyde dialkyl acetals which can be prepared by anodic oxidation of substituted toluenes EP-A-12 240 likewise discloses that ortho-substituted as well as meta- and para-substituted toluenes can be oxidized to the corresponding substituted benzaldehyde dialkyl acetals. This means that, in the case of 4-substituted 1,2-dimethylbenzenes, a product mixture consisting of a 4-substituted 2-methylbenzaldehyde dialkyl acetal and a 5-substituted 2-methylbenzaldehyde dialkyl acetal should be formed.

Due to the fact that they are readily oxidizable, benzaldehydes have only a limited shelf life. Benzaldehyde dialkyl acetals, from which the benzaldehydes are obtained in virtually quantitative yields by hydrolysis, are much more stable compounds for storage.

Benzaldehydes are used, for example according to Ullmann's Encyklopädie der technischen Chemie, 4th Edition, Volume 20, pages 234–236, as scents or scent intermediates. They are also employed as intermediates for crop protection agents, dyes or drugs. The use in particular of 4-substituted 2-methylbenzaldehydes as drug intermediates is mentioned in, for example, BE-A 816 463.

According to DE-A 37 13 732, benzaldehyde dialkyl acetals are also used in perfumery. Their advantage over the free aldehydes is their substantially greater stability in nonacidic media.

It is an object of the present invention to provide novel compounds which lead to improved active ingredients or to changing fragrance notes.

We have found that this object is achieved by novel 2-methylbenzaldehyde dialkyl acetals of the general formula I

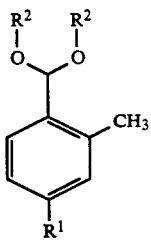

where $R^1$ is $C_3-C_{20}$-alkyl or $C_1-C_{12}$-alkoxy and $R^2$ is $C_1-C_8$-alkyl, with the proviso that R is not methoxy when $R^2$ is methyl, and their preparation and their use for the preparation of 2-methylbenzaldehydes.

The substituents in the compounds of the formulae I, II and III have the following meanings: $R^1$ is $C_3-C_{20}$-alkyl, preferably $C_3-C_8$-alkyl, such as n-propyl, isopropyl, n-butyl, isobutyl, sec-butyl, tert-butyl, n-pentyl, isopentyl, tert-amyl, n-hexyl, n-heptyl or n-octyl, particularly preferably $C_4-C_8$-alkyl, such as n-butyl, isobutyl, sec-butyl, tert-butyl, n-pentyl, isopentyl, tert-amyl, n-hexyl, n-heptyl or n-octyl, or $C_1-C_{12}$-alkoxy, preferably $C_1-C_6$-alkoxy, such as methoxy, ethoxy, n-propoxy, isopropoxy, n-butoxy, isobutoxy, secbutoxy, tert-butoxy, n-pentyloxy or n-hexyloxy, and $R^2$ is $C_1-C_8$-alkyl, such as methyl, ethyl, n-propyl, isopropyl, n-butyl, isobutyl, sec-butyl, tert-butyl, n-pentyl, isopentyl, tert-amyl, n-hexyl, n-heptyl or n-octyl, preferably $C_1-C_4$-alkyl, such as methyl, ethyl, n-propyl, n-butyl or tert-butyl, with the proviso that $R^1$ is not methoxy when $R^2$ is methyl.

Preferred alcohols of the formula $R^2OH$ are those of 1 to 8 carbon atoms, preferably 1 to 4 carbon atoms. Methanol and ethanol are particularly preferred.

In this process, 4-substituted 2-methylbenzaldehyde dialkyl acetals can be prepared particularly advantageously from readily available 4-substituted 1,2-dimethylbenzenes in one stage in high yields and selectivities.

A further advantage of this process is that no expensive purification measures are required since the 5-substituted 2-methylbenzaldehyde dialkyl acetal positional isomers, which are difficult to separate off, are greatly suppressed.

The novel compounds I can be prepared by electrochemical methods in the electrolysis cells conventionally used in industry. Undivided flow-through cells are preferably used.

Suitable anodes are, for example, noble metal electrodes, such as platinum, or oxide electrodes, such as $Ti/RuO_x$, $RuO_2$ or $Cr_2O_3$. Graphite is the preferred anode material.

Suitable cathodes are, for example, steel, iron, nickel, copper, zinc and carbon, as well as noble metals, such as platinum. Graphite is the preferred cathode material.

The electrolyte is composed of the starting compound of the formula II, the alcohol $R^2OH$ and an auxiliary electrolyte.

Suitable auxiliary electrolytes are neutral salts, acids and bases. Examples of neutral salts are fluorides, such as KF, sulfonates, such as $NaSO_3Ph$, sulfates, such as $(CH_3)_4NSO_4CH_3$, tetrafluoborates, such as $NaBF_4$, phosphates and phosphonates. Examples of acids are sulfuric acid, alkylsulfonic acids and arylsulfonic acids, such as methylsulfonic acid or benzenesulfonic acid. The bases used are, for example, alcoholates, such as $NaOCH_3$, or hydroxides, such as KOH.

The electrolyte has, for example, the following composition:
from 1 to 49, preferably from 5 to 30, % by weight of a compound of the formula II,
from 50 to 99, preferably from 70 to 95, % by weight of $R^2OH$ and
from 0 1 to 5, preferably from 0.2 to 3, % by weight of an auxiliary electrolyte.

In the novel process, the current density can be chosen within wide limits, for example from 0.5 to 25, preferably from 1 to 10, $A/dm^2$.

The temperatures may likewise be varied within wide limits. Thus, the oxidations may be carried out at from 0° to 100° C., preferably from 20° to 80° C.

The electrolysis temperature is dependent on, inter alia, the alcohol $R^2OH$ Temperatures below the boiling point of the alcohol $R^2OH$ are generally employed.

The electrolyses are preferably carried out at atmospheric pressure, but may also be effected at from 0.09 to 10 bar. Owing to the associated elevation of the boiling point, it is also possible, for example, to carry out the electrolysis in methanol at above 60° C.

The starting compounds of the formula II can be converted to a very substantial extent. Unconverted 4-substituted 1,2-dimethylbenzene and the 4-substituted 2-methylbenzyl alkyl ether intermediate can be recycled to the electrolysis. The electrolysis can be carried out either continuously or batchwise. The discharged electrolysis mixtures are worked up by a conventional method, preferably by distillation.

The novel 2-methylbenzaldehyde dialkyl acetals obtained by the claimed process are used, for example, as stable forms of 2-methylbenzaldehydes. They can be readily hydrolyzed to the corresponding benzaldehydes of the general formula III

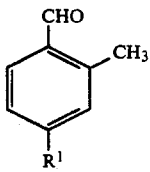
(III)

where $R^1$ is $C_3$-$C_{20}$-alkyl or $C_1$-$C_{12}$-alkoxy. The hydrolysis of the diacetals is carried out by a conventional method, for example by simple heating in water with the addition of a catalytic amount of acid at from 40° to 95° C. Some of the 2-methylbenzaldehydes prepared in this manner are novel, for example p-tert-amyl-2-methylbenzaldehyde.

The novel compounds I have the following fragrance notes:

4-tert-Butyl-2-methylbenzaldehyde dimethyl acetal: tobacco/leather-like phenolic fragrance 4-tert-Amyl-2-methylbenzaldehyde dimethyl acetal: sweet phenolic, minty-fruity fragrance with a ginger note.

The fragrance notes disclosed in DE-A-37 13 732 for benzaldehyde dialkyl acetals are:

Benzaldehyde dimethyl acetal: sweetish green
Benzaldehyde diethyl acetal: sweet, wild and green
Anisaldehyde dimethyl acetal: tangy green, slightly floral
Anisaldehyde diethyl acetal: floral sweet, slightly green
3-tert-Butyl-4-methoxybenzaldehyde dimethyl acetal: floral sweet with an earthy secondary note
3-tert-Butyl-4-methoxybenzaldehyde diethyl acetal: persistent green note.

EXAMPLES

EXAMPLE 1

| | |
|---|---|
| Electrosynthesis of dimethyl acetal | 4-methoxy-2-methylbenzaldehyde |
| Apparatus: | Undivided cell with 11 bipolar electrodes |
| Anodes: | Graphite |
| Electrolyte: | 250 g (1.838 mol) of 4-methoxy-1,2-dimethylbenzene, 30 g of $NaSO_3C_6H_5$, 2750 g of methanol |
| Cathodes: | Graphite |
| Current density: | 3.4 A/dm² |
| Electrolysis temperature: | 23° C. |
| Electrolysis with 4.75 F/mol of 4-methoxy-1,2-dimethylbenzene. | |

The electrolyte is pumped through the cell at 200 l/h during the electrolysis. Following electrolysis, the methanol is distilled off at atmospheric pressure up to a bottom temperature of 120° C., the conductive salt is filtered off and the filtrate is purified by distillation under reduced pressure. 193 g (54%) of 4-methoxy-2-methylbenzaldehyde dimethyl acetal of boiling point 130° C./6 mbar are obtained.

EXAMPLE 2

Electrosynthesis of 4-tert-butyl-2-methylbenzaldehyde dimethyl acetal 4-tert-Butyl-1,2-dimethylbenzene is oxidized in the electrolysis cell described in Example 1 under the conditions stated there and using 9 bipolar electrodes.

| | |
|---|---|
| Electrolyte: | 4,317 g (26.648 mol) of 4-tert-butyl-1,2-dimethylbenzene, 144 g of $KSO_3C_6H_5$ and 24,320 g of methanol |
| Electrolysis temperature: | 36° C. |

Electrolysis with 5.8 F/mol of 4-tert-butyl-2-methylbenzaldehyde dimethyl acetal The electrolyte was worked up as described in Example 1. Purification by distillation under reduced pressure gives 4,065 g (69%) of 4-tert-butyl-2-methylbenzaldehyde dimethyl acetal of boiling point 100°–105° C./4 mbar.

EXAMPLE 3a

Electrosynthesis of 4-tert-amyl-2-methylbenzaldehyde dimethyl acetal 4-tert-Amyl-1,2-dimethylbenzene is oxidized in the electrolysis cell described in Example 1 under the conditions stated there.

| | |
|---|---|
| Electrolyte: | 121 g (0.688 mol) of 4-tert-amyl-1,2-dimethylbenzene, 15 g of $NaSO_3C_6H_5$ and 2,864 g of methanol |
| Electrolysis temperature: | 25° C. |

Electrolysis with 6 F/mol of 4-tert-amyl-1.2-dimethylbenzene

Working up is carried out as described in Example 1. After purification by distillation under reduced pressure 12.1 g (10%) of unconverted educt, 21.9 g (15%) of 4-tert-amyl-2-methylbenzyl methyl ether and 63.3 g (39%) of 4-tert-amyl-2-methylbenzaldehyde dimethyl acetal of boiling point 124°–126° C./8 mbar are obtained.

EXAMPLE 3b

Preparation of 4-tert-amyl-2-methylbenzaldehyde 56 g of 4-tert-amyl-2-methylbenzaldehyde dimethyl acetal are boiled for 1 hour with 170 g of 1% strength sulfuric acid. The methanol formed is distilled off and the organic phase is separated off and dried over $Na_2SO_4$. 35 g (80%) of 4-tert-amyl-2-methylbenzaldehyde are obtained.

EXAMPLE 4

Electrosynthesis of 2,4-dimethylbenzaldehyde dimethyl acetal

Pseudocumene (1,2,4-trimethylbenzene) is oxidized in the electrolysis cell described in Example 1 under the conditions stated there.

| | |
|---|---|
| Electrolyte: | 1,350 g (11.250 mol) of 1,2,4-trimethylbenzene, 90 g of $NaSO_3C_6H_5$ and 7,560 g of methanol |
| Electrolysis temperature: | 25° C. |

Electrolysis with 4.75 F/mol of 1,2,4-trimethylbenzene

Working up is carried out as described in Example 1. After purification by distillation under reduced pressure, 902.6 g (45%) of 2,4-dimethylbenzaldehyde di7 methyl acetal of boiling point 65°–70° C./2 mbar are obtained.

We claim:

1. A process for the preparation of a 2-methylbenzaldehyde dialkyl acetal of the formula

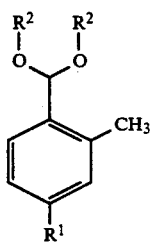
(I)

where $R^1$ is $C_3$–$C_{20}$-alkyl or $C_1$–$C_{12}$-alkoxy and $R^2$ is $C_1$–$C_8$-alkyl, with the proviso that $R^1$ is not methoxy when $R^2$ is methyl, which process comprises:

electrochemically oxidizing a 1,2-dimethylbenzene of the formula

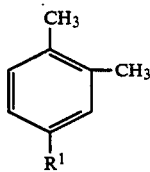
(I)

where $R^1$ has the above-mentioned meanings, with an alcohol $R^2$—OH, where $R^2$ has the above-mentioned meanings, and an auxiliary electrolyte.

2. A process as claimed in claim 1, wherein the oxidation of compound (II) with the alcohol $R^2$—OH is carried out by electrolysis of the reactants as an electrolyte in an electrolytic cell at a current density of about 0.5 to 25 A/dm$^2$ and at a temperature of about 0° to 100°.

3. A process as claimed in claim 2, wherein the electrolysis is carried out using a graphite anode and a graphite cathode.

4. A process as claimed in claim 2, wherein the electrolyte has the following composition:
from 1 to 49% by weight of the compound (II);
from 50 to 99% by weight of the alcohol $R^2$—OH; and
from 0.1 to 5% by weight of the auxiliary electrolyte.

5. A process as claimed in claim 2, wherein the electrolyte has the following composition:
from 5 to 30% by weight of the compound (III);
from 70 to 95% by weight of the alcohol $R^2$—OH; and
from 0.2 to 3% by weight of the auxiliary electrolyte.

6. A process as claimed in claim 2, wherein the alcohol used in methanol.

7. A process as claimed in claim 2, wherein the alcohol used is ethanol.

8. A process as claimed in claim 1, wherein the 2-methylbenzaldehyde dialkyl acetal (I) is separated as a stable product and then converted by hydrolysis into the corresponding 4-substituted-2-methylbenzaldehyde of the formula

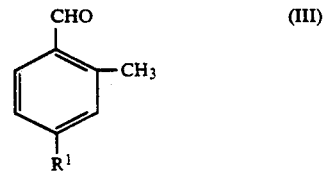

where $R^1$ has the same meaning given above.

9. A process as claimed in claim 8, wherein the acetal (I) is hydrolyzed by heating in water with the addition of a catalystic amount of acid and at a temperature of from 40° to 95° C.

10. A process as claimed in claim 8, wherein $R^1$ is $C_3$–$C_8$-alkyl or $C_1$–$C_6$-alkoxy.

11. A process as claimed in claim 8, wherein $R^1$ is tert.-amyl.

* * * * *

UNITED STATES PATENT AND TRADEMARK OFFICE
CERTIFICATE OF CORRECTION

PATENT NO.   : 5,208,384
DATED        : May 4, 1993
INVENTOR(S)  : Dieter Hermeling It is certified that error appears in the above-identified patent and that said Letters Patent is hereby corrected as shown below:

IN THE CLAIMS:
   Column 5, line 36
     Claim 1, line 8 (disregarding the formulas I and II):

cancel "with" and substitute --in the presence of--.
   Column 5, line 43
     Claim 2, last line: after "100°", insert --C--.
   Column 6, line 12
     Claim 5, line 3: cancel "(III)" and substitute --(II)--.
   Column 6, line 17
     Claim 6, line 2: cancel "in" and substitute --is--.

Signed and Sealed this

First Day of March, 1994

Attest:

BRUCE LEHMAN

Attesting Officer      Commissioner of Patents and Trademarks